[US006255350B1](#)

United States Patent
Jon et al.

(12) 
(10) Patent No.: US 6,255,350 B1
(45) Date of Patent: *Jul. 3, 2001

(54) STABILIZED CONCENTRATES OF WATER UNSTABLE AZA COMPOUNDS AND O/W MINIEMULSIONS THEREOF

(75) Inventors: Domingo I. Jon, New York, NY (US); Donald I. Prettypaul, Englewood, NJ (US); Matthew J. Benning, Highland Lakes, NJ (US); Kolazi S. Narayanan, Wayne, NJ (US); Robert M. Ianniello, Oak Ridge, NJ (US)

(73) Assignee: ISP Investments Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/169,697

(22) Filed: Oct. 9, 1998

Related U.S. Application Data

(60) Provisional application No. 60/061,944, filed on Oct. 14, 1997.

(51) Int. Cl.$^7$ ............................. A01N 37/00; A01N 31/00; A01N 33/00; A01N 35/00; A01N 43/00
(52) U.S. Cl. ...................... 514/588; 424/405; 504/116.1; 504/118; 504/189; 504/358; 514/65; 514/183; 514/506; 514/557; 514/631; 514/646; 514/675; 514/706; 514/715; 514/740; 514/741; 514/769; 514/770; 514/772; 514/788; 514/937; 514/938; 514/939; 514/943; 514/970; 514/975
(58) Field of Search ............................. 424/405; 504/116, 504/116.1, 118, 189, 358; 514/579, 788, 938, 942, 970, 65, 68, 70, 71, 72, 73, 183, 210.01, 210.02, 210.03, 210.04, 210.05, 210.07, 210.09, 210.1, 210.16, 210.17, 210.18, 210.19, 210.2, 222.2, 222.5, 222.8, 223.8, 224.2, 226.8, 227.2, 227.5, 227.8, 241, 242, 243, 245, 246, 247, 248, 249, 252.01, 252.02, 252.03, 252.05, 252.1; 514/252.11, 252.12, 252.13, 252.14, 252.18, 252.19, 253.01, 253.09, 253.1, 253.11, 253.12, 254.01, 254.02, 254.04, 254.06, 254.07, 255.01, 255.02, 255.05, 255.06, 256, 257, 258, 269, 272, 274, 275, 277, 279, 315, 316, 317, 318, 326, 327, 328, 329, 330, 331, 332, 333, 335, 336, 340, 341, 342, 343, 344, 345; 514/348, 349, 350, 351, 352, 354, 357, 359, 365, 366, 367, 369, 370, 371, 372, 373, 385, 387, 403, 405, 430, 432, 433, 434, 448, 506, 510, 519, 520, 521, 523, 524, 557, 576, 577, 588, 595, 596, 646, 656, 657, 675, 676, 677, 378, 679, 680, 681, 706, 708, 709, 715, 716, 717, 769, 770, 772, 937, 939, 943, 975, 631, 740, 741

(56) References Cited

U.S. PATENT DOCUMENTS

| | | | |
|---|---|---|---|
| 4,438,137 | * | 3/1984 | Allan ..................................... 514/631 |
| 5,071,463 | * | 12/1991 | Narayanan et al. .................. 504/365 |
| 5,707,638 | * | 1/1998 | Losel et al. ........................... 424/407 |
| 5,731,264 | * | 3/1998 | Narayanan et al. .................. 504/363 |
| 5,968,990 | * | 10/1999 | Jon et al. ............................. 514/788 |
| 6,024,972 | * | 2/2000 | Narayanan et al. .................. 424/405 |

FOREIGN PATENT DOCUMENTS

99/19256 * 4/1999 (WO) .

* cited by examiner

*Primary Examiner*—Jose G. Dees
*Assistant Examiner*—Frank I Choi
(74) *Attorney, Agent, or Firm*—Marilyn J. Maue; William J. Davis; Walter Katz

(57) ABSTRACT

This invention relates to a single phase emulsifiable concentrate composition comprising (a) between about 0.05 and about 25 wt. % of a biologically, fungicidally and/or herbicidally active aza compound; (b) between about 2 and about 40 wt. % of a lactam selected from the group of N-methyl pyrrolidone, N-methyl caprolactam, a $C_8$ to $C_{18}$ alkyl pyrrolidone, a $C_8$ to $C_{18}$ caprolactam and a mixture thereof; (c) between about 2 and about 20 wt. % of a moisture scavenging agent selected from the group consisting of a liquid molecularly hindered carbodiimide, a molecular sieve or a mixture thereof and (d) between about 10 and about 80 wt. % of a mixture of at least two non-ionic surfactants having an overall hydrophilic/lipophilic balance (HLB) above 7. The invention also relates to the stable oil-in-water (o/w) miniemulsions prepared from the above by dilution to between about 40 and about 99.99 wt. % water for a "pour on", dip or spray solution useful in the treatment of animals or plants.

19 Claims, No Drawings

STABILIZED CONCENTRATES OF WATER UNSTABLE AZA COMPOUNDS AND O/W MINIEMULSIONS THEREOF

This application is a continuation-in-part based upon the Provisional Application, Serial No. 60/061,944, filed on Oct. 14, 1997 in the names of the same inventors.

DEFINITION OF TERMS

For the purposes of this disclosure, the following terms are defined as follows. The miniemulsion herein employed is a microemulsion having a micellular droplet size less than 400 nm which miniemulsion is derived from the dilution of the present water free concentrate composition. This miniemulsion is employed as a clear o/w liquid which is stabilized for extended storage or immediate use.

The active aza compounds referred to herein are active herbicidal or pesticidal compounds containing the aza group $$-N-C-N-$$

and includes compounds having the structure $$R_1-(X)-R_2$$

wherein one of $R_1$ and $R_2$ is a sulfur- and/or nitrogen-containing heterocyclic radical containing 3 to 5 carbon atoms in a 4 to 6 membered heterocyclic ring and alkenylphenyl, and the other of $R_1$ and $R_2$ is the same or is amidosulfuron, phenyl, sulfonylphenyl, phenyloxy, phenoxysulfonyl, or phenylamino where said phenyl radicals and heterocyclic radicals are optionally substituted with lower alkyl, halo, haloalkyl, cyano, $C_1$ to $C_4$ alkyl ether, $C_1$ to $C_4$ester, carboxy, ketone, and/or amino and X is $$-N-CO-N- \quad \text{or} \quad -N=C-N-$$
$$\phantom{-N-CO-N-}R_3 \phantom{xx} R_4 \phantom{xxxxxxxx} R_5 \phantom{x} R_6$$

where $R_3$, $R_4$, $R_5$ and $R_6$ are each individually selected from the group of hydrogen, lower alkyl, cyano and amino. Specific examples of some aza compounds are disclosed in U.S. Pat. No. 5,731,264 and are incorporated herein by reference.

Lower alkyl is the radical containing 1 to 4 carbon atoms.

The hydrophilic/hydrophobic balance is expressed as HLB and the HLB of the present miniemulsion is between 7 and 20.

The molecular sieve is a zeolite having an open network structure and pore openings sufficient to absorb water molecules.

The emulsifying agent or surfactant emulsifier mixture is amphipathic containing hydrophilic and hydrophobic portions which can be adjusted by the degree of alkoxylation to meet the needs of the active ingredient selected. In general, the lower the degree of alkoxylation, the more hydrophobic the emulsifier; conversely, the higher the degree of alkoxylation, the more hydrophilic the emulsifier.

BACKGROUND OF THE INVENTION

Formulations of various types, including standard emulsions, suspensions, dispersions and dusts have been developed for delivery of biologically active components on animals and plants for control of insects and weeds. For ecological reasons, liquid, sprayable formulations are most sought after. However, many highly active and desirable aza compounds are totally unstable in water and hydrolyze to inactive metabolites. The high reactivity of Amitraz and sulfonyl urea are cases in point.

Accordingly, the use of these valuable chemicals has been limited to dusts or solutions employing expensive hydrophobic solvents or solvent mixtures. In the search for water stabilized Amitraz concentrate formulations, the use of 1,5-di(2,6-diisopropylphenyl) carbodiimide and or dicyclohexyl carbodiimide have shown some stabilizing affect (see U.S. Pat. No. 4,438,137). However, upon dilution of the concentrate with water in amounts useful for spraying or "pour on" solutions, a significant amount of inactive metabolites are formed; hence, economical use of these active ingredients in a water base is not achieved.

Accordingly, it is an object of this invention to provide a stabilized, water based miniemulsion of a hydrolyzable, biologically active aza compound which can be stored for extended periods without degradation.

Another object of this invention is to provide an aqueous solution of a concentrate containing a high load of the hydrolyzable aza compound.

Still another object is to provide a water solution containing stabilized aza compounds which employ biodegradable and environmentally safe carriers.

Yet another object concerns the preparation of a non-aqueous concentrate of the said hydrolyzable compound which has unique properties and produces miniemulsions of improved efficacy.

These and other objectives of the invention will become apparent from the following description and disclosure.

SUMMARY OF THE INVENTION

The above objects are achieved by instant emulsifiable concentrate composition and by the stabilized water diluted miniemulsion prepared therefrom. In accordance with this invention, there is provided an anhydrous liquid concentrate composition of (a) between about 0.05 and about 25 wt. % of a pesticidally active aza compound; (b) between about 2 and about 40 wt. % of a lactam selected from the group of N-methyl pyrrolidone (NMP), N-methyl caprolactam, a $C_8$ to $C_{18}$ alkyl pyrrolidone, a $C_8$ to $C_{18}$ alkyl caprolactam and a mixture thereof; (c) between about 2 and about 20 wt. % of a water scavenging agent selected from the group consisting of a hindered carbopolyimide compound and a molecular sieve and mixtures thereof and (d) between about 10 and about 80 wt. % of a mixture of at least two non-ionic surface active emulsifiers having an HLB of from about 7 to about 20, most preferably having an HLB of from about 7.5 to 11. The preferred composition of the concentrate contains from about 8 to about 15 wt. % (a); from about 15 to about 30 wt. % $C_8$ and/or $C_{12}$ alkyl pyrrolidone optionally containing up to 14 wt. % NMP, most preferably not more than 5 wt. % NMP; from about 5 to about 15 wt. % (c) and from about 65 to about 78 wt. % (d).

The concentrate, when diluted with up to 99.99 wt. % water (a dilution of $10^{-4}$ of the active component), is ideally contained in a miniemulsion having a droplet size below 450 nm. In particular, the Amitraz miniemulsion undergoes no hydrolyzation for more than the 3 day period observed and is a clear water white liquid as opposed conventional emulsions observed over the same period having varying degrees of opacity associated with larger suspended particles. Optionally, other additives or excipients can be included in the above compositions, either as concentrate additives or as miniemulsion additives.

For example when needed to maintain an acidic medium, i.e. at a pH of 3–5, up to about 5 wt. % of a hydrophobic, surface active acid, such as an ethoxylated phosphate ester or e.g. citric acid, can be added as a buffer to the concentrate composition or the subsequently formed o/w miniemulsion. A wetting and spreading agent such as a silicone based surfactant, e.g. Heptamethyl trisiloxane (SILWET® L77, Osi Specialties Inc.) can also be added in an amount up to about 10%, preferably not more than 5%. Other additives, can also be incorporated in the mixtures, such as for example a stabilizer and/or a cosolvent to promote the solubility of the active component in the hydrophobic portion of the emulsion in cases where high load of active is desired. Examples of suitable cosolvents include butyrolactone (BLO), propylene carbonate, furfural, furfural ether, the acetic acid ester with a $C_7$ rich oxoalcohol (EXXATE® 700), and the like.

The anhydrous Amitraz concentrate of this invention is remarkably stable and undergoes less than 10% decomposition for at least the observed period of 2 weeks when stored at 25° C. over or in the presence of a molecular sieve or a carbodiimide. The miniemulsion of Amitraz is also stable for at least 12 days which is unexpected since prior aqueous formulations show appreciable decomposition of this compound within 6 hours.

DETAILED DESCRIPTION OF THE INVENTION

The clear, water white o/w liquid owes its clarity and stability to the formation of the miniemulsion containing micelle droplets having an average particle size less than about 0.1 micron ($\mu$), preferably less than 0.05$\mu$ at 35° C.

Upon dilution of the present concentrate, the lipophilic pyrrolidone component, in the absence of N-methyl pyrrolidone, interacts in the micelle formation so as to orient the water soluble portions of the emulsifying mixture to the surface of the droplet while itself forming a distinct intermediate, water resistant layer or interface around the encapsulated active ingredient. The strong lipophilic nature of the pyrrolidone component, employed at the interfacial layer, enforces isolation of the active species and provides longer protection against hydrolysis during storage of the o/w miniemulsion. Additionally, the lipophilic pyrrolidone liberates the encapsulated active component on the surface of the animal or plant when applied thereon as a spray or pour-on solution; thus increasing the biocidal or pesticidal activity and efficiency of the emulsion.

The active compounds of this invention contain an aza radical and are more particularly defined in the foregoing Definition of Terms. Specific examples of such biologically or herbicidally active compounds include Amitraz, Metsulfuron-methyl, Metsulfuron, Thifensulfuron, Chlorsulfuron, Sulfometuron and the like.

Amitraz has the structure:

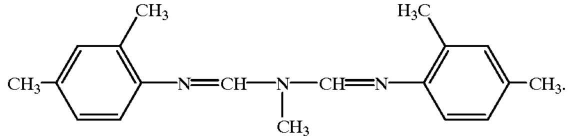

This insecticidal, acaricidal compound has a half life of about 6 hours in water at a pH of 7, and is soluble in water to the extent of 1 mg/liter. The heterocyclic sulfonyl urea, Metsulfuron-methyl, having the structure 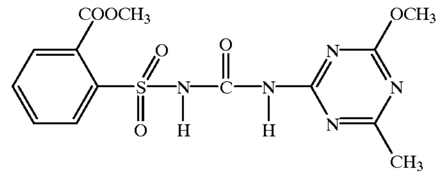 and Metsulfuron having the structure 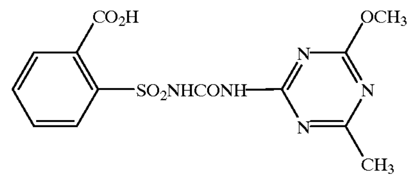 have similar half lives, as do other active aza compounds, such as sulfonyl urea (cyclosulfamuron) and those disclosed in U.S. Pat. No. 5,731,264. Of the above active compounds, Amitraz and Metasulfuron-methyl are preferred.

The preferred active components in concentrates of this invention are clear and remain stable for at least about 8 days at 52° C., and longer when stored in the presence of a stabilizer such as a molecular sieve and/or a hindered carbodiimide. Under these conditions, at least 65% of the active is retained in the concentrate at elevated temperatures. Upon dilution with water the concentrates form effective o/w emulsions which are themselves stable over extended periods, even at elevated temperatures.

Compositions containing the active component of this invention can be applied topically to farm or domestic animals as a "pour on", dip or spray o/w solution to control ectoparasites such as mites, ticks, lice as well as fungi such as mange and other dermal disorders.

It is found that the bioactivity of the aza compounds may be promoted by positive addition of up to 40% wt. %, of an iso-octyl ester, 4-chloro-2-methylphenoxy acetic acid or up to 6 wt. % of a pyrethroid, alone or in admixture with a phosphate buffer, e.g. 9.75 ethoxylated phosphate ester RHODAFAC® RS 710, the alkyl phenol ethoxylated ester RHODAFAC RM 710, both supplied by Rhone Poulenc. Preferably, the concentrate contains up to 6 wt. %, based on the weight of the aza component, of the pyrethroid activity promoter. Specific pyrethroids which are preferred activity promoters include deltamethrin and cypermethrin. The additional use of a stabilizer for the aza compound, up to about 12%, of for example 2,2',6,6'-tetraisopropyl diphenyl carbodiimide (STABAXOL® I from Rhein Chemie), can also increase activity.

The amphipathic emulsifying agent in the concentrate of this invention is a mixture of at least two nonionic surfactants comprising between about 35 and about 75% of a 5–60 ethoxy unit ethoxylated mineral or vegetable oil or triglyceride such as castor oil, soybean oil, linseed oil, rapeseed oil etc. and represents the lipophilic portion of the mixture having an HLB for example of 5–11. The lipophilic portion can contain 1–3 emulsifiers of this type. This lipophilic emulsifier portion is combined with between about 25 and about 45% of an 5–60 ethoxy unit ethoxylated aliphatic condensate derived from a saturated or mono- or polyunsaturated acid to form an ester as the hydrophilic portion of the mixture having a HLB of for example 12–16. This hydrophilic portion may also contain 1–3 emulsifier species of this type. The ethoxylated emulsifier can also be derived from acids which include sorbic, oleic, stearic and palmitic acids. Alternatively, other hydrophilic emulsifiers such as anionic alkyl phosphates and sulfonate esters can be used as well as ethyloxylated, reduced sugars, saturated ethoxylated sorbitan and the like. Of these, castor oil of 12–40 ethoxy units (ALKAMULS® EL and ALKAMULS CO 15, both from Rhone Poulenc), are preferred as the lipophilic emulsifier and a sorbitan mono-, di-, or tri-oleate, most particularly the monooleate, (ALKAMULS PSMO 20) and $C_8$ to $C_{12}$ alkyl phosphates are preferred as the hydrophilic emulsifier. In this preferred lipophilic/hydrophilic emulsifier mixture, between about 65 and about 75 wt. % is oil and between about 30 and about 35 wt. % is the hydrophilic emulsifier.

In the present concentrate composition it is critical for the formation of an o/w emulsion that the emulsifiers in the mixture be combined to provide an overall HLB of at least 7 up to 20, most preferably 8–11. An HLB below 7 would result in a w/o emulsion or an emulsion containing large droplets which is undesirable for spray applications. Further, oil as the continuous phase is not as ecologically acceptable as water.

An important component of the present composition is the lipophilic alkyl pyrrolidone which interacts with the emulsifier mixture to form an interface between the active component and the water scavenger during the formation of micelles in the product miniemulsion. Thus, the active component is retained ip the micellar droplet core with outer protective layers surrounding it. This phenomena occurs even after high dilution of the concentrate, e.g. with from about 10 to about 1,000 or more parts of water to concentrate. Further the pyrrolidone component delays the hydrolysis of the carbodiimide to the corresponding urea by reason of its intermixture with the hydrophobic portion in the emulsifier mixture which portion in turn is intermixed with the hydrophilic surface of the droplet. In this way the protective outer layers of the micelle are retained for a longer time period.

The carbopolyimide component of the concentrate is one wherein the terminal organic substituent on the nitrogen atom is a non-functional aliphatic, cycloaliphatic, heterocyclic or aromatic group which may be polymeric or non-polymeric. Of these the carbodiimides hindered by a substituted group on the nitrogen atom are most useful. Examples of such substitution groups include alkylphenyl, sulfonyl ester sulfonamides, imido, imido esters, sulfonyl urea groups as bis(hydroxyphenyl) imide,

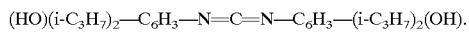
(HO)(i-C$_3$H$_7$)$_2$—C$_6$H$_3$—N=C=N—C$_6$H$_3$—(i-C$_3$H$_7$)$_2$(OH).

Of the above hindered carbodiimide compounds, tetraisopropyldiphenyl carbodiimide is preferred since, it is hydrolyzed to the corresponding biodegradable tetraisopropyl diphenyl urea. The following equation illustrates the hydrolysis of tetraisopropyl diphenyl carbodiimide.

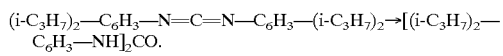
(i-C$_3$H$_7$)$_2$—C$_6$H$_3$—N=C=N—C$_6$H$_3$—(i-C$_3$H$_7$)$_2$→[(i-C$_3$H$_7$)$_2$—C$_6$H$_3$—NH]$_2$CO.

Molecular sieve particles can,be employed in the presence or in place of the hindered carbodiimide liquid to maintain anhydrous conditions and to absorb small and trace amounts of water initially introduced in the separate components of the concentrate. When water initially in the concentrate approaches 0.1%, up to 15% molecular sieve particles can be added to the concentrate as a powder or can be contacted with the concentrate or components thereof as a filter or a membrane barrier to maintain anhydrous conditions during the mixing of components and storage of the condensate. Generally, when the scavenging agent carbodiimide is employed alone or in combination with the molecular sieve, it is contacted with the other components before or during the mixing step prior to the introduction of the active component.

The zeolite sieve can be regenerated for the treatment of subsequent concentrate compositions by decanting or filtering off the supernate liquid and drying the remaining solid particles separated from the anhydrous concentrate before being recycled for use in the manufacturing process.

The method of forming the condensate may employ any order of component addition.

Particularly useful concentrate compositions of this invention suitable for the preparation of an o/w emulsion are the following:

Formulation I

| INGREDIENT | WT. % | MOST PREFERRED | BEST |
|---|---|---|---|
| (1) Active Chemical | 3–25 | 8–15 | 10 |
| (2) Optional Pyrethroid | 0–6 | 1–4 | 3 |
| (3) 15 EO Castor Oil | 35–55 | 38–50 | 40 |
| (4) N-octyl Pyrrolidone | 10–40 | 15–30 | 25 |
| (5) 20 EO sorbitan monooleate | 10–35 | 20–30 | 25 |
| (6) Molecular Sieve | 5–20 | 7–15 | 9 |
| (7) RHODAFAC RS 10 | 0–5 | 0.5–3 | 0.9 |
| (8) SILWET L 77 | 0–7 | 0.5–5 | 2 |
| (9) N-methyl Pyrrolidone | 0–20 | 1–14 | 2 |
| The HLB of the concentrate is | 8–11 | 10 | 9.5 |

Formulation II

| Ingredient | Wt. % |
|---|---|
| Metsulfuron-methyl | 0.34 |
| MCPA iso-octyl ester* | 38.09 |
| Agsol Ex 8** | 0.50 |
| BLO | 8.98 |
| Exxate 700 | 27.52 |
| Rhodafac RM 710 (Gafac RM 710) | 3.81 |
| TEA | 0.76 |
| Alkamuls EL 719 (Castor oil, 40 EO) | 15.24 |
| Stabaxol I | 4.76 |

*(4-chloro-2-methylphenoxy) acetic acid
**N-octylpyrrolidone

Formation III

| Ingredient | Wt. % |
|---|---|
| Metsulfuron-methyl | 0.34 |
| MCPA iso-octyl ester | 35.00 |
| Agsol Ex 8 | 0.50 |
| BLO | 9.46 |
| Exxate 700 | 27.00 |
| Rhodafac RM 710 | 4.00 |
| TEA | 0.80 |
| Alkamuls EL 719 | 15.00 |
| Molecular Sieve 4A | 8.00 |

To form the present miniemulsion and to test stability thereof, the above concentrate composition is diluted with 10, 100, 1,000 and 10,000 parts of water. All provided clear o/w miniemuslsions.

Having generally described the invention, reference is now had to the accompanying Examples, which illustrate preferred embodiments, and comparative data but which are not to be construed as limiting to the scope of the invention as is more broadly defined in the appended claims.

EXAMPLE 1

Following ingredients are mixed in a 4 oz narrow mouth glass bottle using a magnetic stirrer for a period of 60 minutes 0.25 g of Agsol Ex 8, 4.2 g of BLO, 19 g of Exxate 700, 2 g of Rhodafac RM 710, 0.4 g TEA, 8 g Alkamuls EL 719, 20 g of MCPA Iso-octyl ester and 3 g Stabaxol I. 0.15 g of Metsulfuron-methyl is, then, added to this homogeneous mixture. The sample is mixed further in a circular wheel to dissolve the active ingredient. The sample is stored at 52° C. for 8 days. HPLC analysis shows a retention of 45% or better Metsulfuron-methyl after 8 days.

EXAMPLE 2

Example 1 is repeated without Stabaxol I and pretreated with 10% molecular sieves 4A for 2 days. The water content in the mixture is determined at 0.01% using the Karl Fischer method with a Mitsubishi Moisturemeter model CA-02. 0.15 g of Metsulfuron-methyl is, then, added to the mixture. The sample is stored at 52° C. for 8 days. HPLC analysis shows a retention of 44% or better Metsulfuron-methyl after 8 days.

EXAMPLE 3

Example 1 is repeated without Stabaxol I and with the addition of 0.17 g of Metsulfuron-methyl to the mixture. HPLC analysis shows a retention of 6% Metsulfuron-methyl after 8 days.

EXAMPLE 4

Following ingredients are mixed in a 4 oz narrow mouth glass bottle using a magnetic stirrer for a period of 60 minutes 18 g of Agsol Ex 8, 36 g of Alkamuls CO-15, 22 g of Alkamuls PSMO-20, and 10 g of Stabaxol I. 10 g of amitraz are, then, added to this homogeneous mixture. The sample is mixed further in a circular wheel to dissolve the active ingredient. 50 g of the sample are stored at 52° C. for 14 days. HPLC analysis shows a retention of 85% amitraz after 14 days.

The remaining 46 g sample of concentrate are diluted at 1:10 ratio with 1000 ppm hard water. The diluted sample remains physically stable and clear when kept at room temperature for 12 days. HPLC analysis shows a retention of 95% or higher after 12 days.

EXAMPLE 5

Following ingredients are mixed in a 4 oz narrow mouth glass bottle using a magnetic stirrer for a period of 60 minutes 21 g of Agsol Ex 8, 40 g of Alkamuls CO-15, and 24 g of Alkamuls PSMO-20. 10 g of molecular sieves 4A are introduced to the homogeneous mixture in the stoppered bottle and let it stand for 2 days. The water content in the mixture is determined at 0.08% using the Karl Fischer method with a Mitsubishi Moisturemeter model CA-02 10 g of amitraz is, then, added to the mixture, and the sample mixed further in a circular wheel to dissolve the active ingredient. 50 g of the sample are stored at 52° C. for 21 days. HPLC analysis shows a retention of 86% amitraz after 21 days.

The remaining 45 g sample of concentrate are diluted at 1:5, 1:10, 1:20, 1:100 ratios with 1000 ppm hard water. The diluted sample remains physically stable and clear when kept at 23° C. for 3 days. HPLC analysis shows a retention of 90% or higher after 4 days.

EXAMPLE 6

Example 4 is repeated without the addition of molecular sieves 4A and with the addition of 10 g of amitraz to the mixture. HPLC analysis of the concentrate shows a retention of 1% amitraz after 4 days.

EXAMPLE 7

Following ingredients are mixed in a 4 oz narrow mouth glass bottle using a magnetic stirrer for a period of 60 minutes 19.9 g of Agsol Ex 8, 39 g of Alkamuls CO-15, 24.3 g of Alkamuls PSMO-20 and 0.83 g of Rhodafac RS 710. 10 g of molecular sieves 4A are introduced to the homogeneous mixture in the stoppered bottle and let it stand for 2 days. The water content in the mixture is determined below 0.1% using the Karl Fischer method with a Mitsubishi Moisturemeter model CA-02 10 g of amitraz and 3 g of deltamethrin is, then, added to the mixture, and the sample mixed further in a circular wheel to dissolve the active ingredient. 50 g of the sample are stored at 52° C. for 20 days. HPLC analysis shows a retention of 78% of amitraz and 60% deltamethrin after 20 days.

The remaining sample of concentrate is diluted at 1:10, and 1:100 ratios with 1000 ppm hard water. The diluted sample remains physically stable and clear when kept at 23° C. for 5 days.

While the concentrates and miniemulsions of this invention have been described in the examples with particular reference to certain and preferred embodiments, it will be understood that many substitutions and modifications can be made therein without departing from the scope of this invention. For example, substitutions can be made in the active component, the disclosed higher alkyl pyrrolidones can also be substituted for the octyl pyrrolidone in the Examples. The concentration compositions can be altered by the addition of other excipients and other lipophilic/hydrophilic emulsifier mixtures can be employed where individual emulsifier species in a mixture of 2 to 4 species may have an HLB of 3 to 20.

What is claimed is:

1. An anhydrous miniemulsion concentrate which forms a stable oil in water emulsion upon dilution, comprising, by weight, (a) between about 0.05 and about 25% of at least one active aza compound selected from the group consisting of Amitraz and an aza compound having the formula:

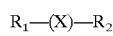

$R_1$—(X)—$R_2$ wherein one of $R_1$ and $R_2$ is alkenylphenyl, aminophenyl or a sulfur- and/or nitrogen-containing heterocyclic radical containing 3 to 5 carbon atoms in a 4 to 6 membered ring and the other of $R_1$ and $R_2$ is the same or is selected from the group consisting of amidosulfuron, phenyl, sulfonylphenyl, phenyloxy and phenyloxysulfonyl where said phenyl radicals and said heterocyclic radicals are optionally substituted with lower alkyl, halo, haloalkyl, cyano, $C_1$ to $C_4$ alkyl ether, $C_1$ to $C_4$ ester, carboxyl, ketone amido and amino and X is:

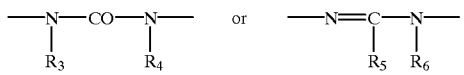

where $R_3$, $R_4$, $R_5$ and $R_6$ are each individually selected from the group consisting of hydrogen, lower alkyl, cyano, and amino, (b) between about 2 and about 40% of a lipophilic lactam selected from the group consisting of $C_8$ to $C_{18}$ N-alkyl pyrrolidone, $C_8$ to $C_{18}$ alkyl caprolactam and a mixture thereof, (c) between about 2 and about 20% of a moisture scavenging agent selected from the group consisting of a hindered carbopolyimide, a molecular sieve and a mixture thereof, and (d) between about 10 and about 80% of a lipophilic/hydrophilic mixture having an overall HLB of 7 to 20, comprising at least two emulsifiers wherein at least two of said emulsifiers in the mixture are non-ionic.

2. The concentrate of claim 1 wherein said active aza compound is a biocide, fungicide and/or phytocide.

3. The concentrate of claim 1 which contains from about 8 to about 15% (a), from about 15 to about 30% of at least one of $C_8$ N-alkyl pyrrolidone and $C_{12}$ N-alkyl pyrrolidone, from about 7 to about 15% (c) wherein said carbopolyimide is a carbodiimide and from about 65 to about 78% (d) and optionally further containing up to 14% of N-methyl pyrrolidone.

4. The concentrate of claim 1 wherein said lipophilic/hydrophilic emulsifier mixture is a lipophilic emulsifier of an ethoxylated mineral or vegetable oil and the hydrophilic emulsifier is an ester of sorbitan wherein said emulsifiers combine to form a mixture of 7.5–11 HLB.

5. The concentrate of claim 4 wherein said ethoxylated vegetable oil is ethoxylated castor oil.

6. The concentrate of claim 4 wherein said ester of sorbitan oleate is sorbitan monooleate.

7. The concentrate of claim 4 wherein said mixture contains between about 35 and about 75 wt. % of said oil and between about 25 and about 45 wt. % of said ester of sorbitan.

8. The concentrate of claim 1 wherein (c) is tetraisopropyl diphenyl carbodiimide.

9. The concentrate of claim 1 wherein said active aza compound is Amitraz, Metsulfuron-methyl, Metsulfuron or a mixture thereof.

10. The concentrate of claim 1 which further comprising up to 6 wt. %, based on weight of the active aza component, of a pyrethroid aza activity promoter.

11. The concentrate of claim 10 wherein said pyrethroid aza activity promoter contains up to 5 wt. % of a phosphate ester buffer.

12. The concentrate of claim 1 further comprising from 0.5 to 7 wt. % of a silicone wetting agent.

13. The concentrate of claim 1 wherein the moisture scavenging agent is the molecular sieve and said concentrate is storage stable.

14. The concentrate of claim 13 wherein the active aza compound is Amitraz, Metsulfuron-methyl, Metsulfuron or a mixture thereof.

15. A o/w miniemulsion comprising a homogeneous mixture of the concentrate of claim 1 and about 40 to about 99.99% by weight of said miniemulsion of water.

16. The o/w miniemulsion of claim 15 wherein the concentration of the active aza compound is between about 0.05 and about 25% by weight with respect to the weight of the concentrate.

17. An aqueous formulation comprising the concentrate of claim 1 diluted with water in a weight ratio of up to 1:10,000 concentrate to water, in the form of an aqueous spray or dip solution for the treatment of a plant or animal.

18. The aqueous formulation of claim 17 wherein said concentrate is diluted with water in a weight ratio of up to 1:200.

19. The aqueous formulation of claim 17 wherein the active component in said concentrate is selected from the group consisting of Amitraz, Metsulfuron-methyl, Metsulfuron and a mixture thereof.

* * * * *